United States Patent [19]

De Jong et al.

[11] Patent Number: 5,386,031

[45] Date of Patent: Jan. 31, 1995

[54] PROCESS FOR THE SYNTHESIS OF 2-AMINO-3,5-DIHYDRO-7-SUBSTITUTED-4H-PYRROLO[3,2-D]PYRIMIDIN-4-ONES

[75] Inventors: Randall L. De Jong, Zealand; Ronald E. Seamans; James R. Zeller, both of Holland, all of Mich.

[73] Assignee: Warner-Lambert Company, Morris Plains, N.J.

[21] Appl. No.: 167,751

[22] Filed: Dec. 15, 1993

[51] Int. Cl.⁶ .................. C07D 487/04; C07B 31/00
[52] U.S. Cl. .................................................. 544/280
[58] Field of Search ........................................ 544/280

[56] References Cited

U.S. PATENT DOCUMENTS

| | | | |
|---|---|---|---|
| 4,923,872 | 5/1990 | Kostlan et al. | 514/258 |
| 4,988,702 | 1/1992 | Kostlan et al. | 514/258 |
| 5,061,707 | 10/1991 | Kostlan et al. | 514/258 |
| 5,281,708 | 1/1994 | Josyula et al. | 544/280 |

OTHER PUBLICATIONS

Journal of Medicinal Chemistry, 36:55–69 (1993) Montgomery J. A. et al.
Journal Medicinal Chemistry, 36: 1847–1854 (1993) Secrist III J. A., et al.
Journal Organic Chemistry, 36:723 (1971) Church, R. F. R., et al.

*Primary Examiner*—Mark L. Berch
*Attorney, Agent, or Firm*—Francis J. Tinney

[57] ABSTRACT

An improved process for the preparation of 2-amino-3,5-dihydro-7-substituted-4H-pyrrolo[3,2-d]pyrimidin-4-ones is described wherein 2,6-diamino-3,5-dihydro-7-substituted-4H-pyrrolo[3,2-d]pyrimidin-4-one is converted to a diazonium salt which is subsequently catalytically hydrogenated to the desired compound, as well as valuable intermediates used in the process.

18 Claims, No Drawings

PROCESS FOR THE SYNTHESIS OF 2-AMINO-3,5-DIHYDRO-7-SUBSTITUTED-4H-PYRROLO[3,2-D]PYRIMIDIN-4-ONES

BACKGROUND OF THE INVENTION

Montgomery J. A., et al., *Journal of Medicinal Chemistry*, 36:55–69 (1993) disclose a series of 9-(arylmethyl) derivatives of 9-deazaguanine useful as inhibitors of purine nucleoside phosphorylase. Additionally, Secrist III J. A., et al., *Journal of Medicinal Chemistry*, 36:1847–1854 (1993) disclose a series of 9-alicyclic and 9-heteroalicyclic derivatives of 9-deazaguanine useful as inhibitors of purine nucleoside phosphorylase. Inhibitors of purine nucleoside phosphorylase may have therapeutic value in the treatment of T-cell proliferative diseases such as T-cell leukemias or lymphomas, in the suppression of host-vs-graft response in organ transplants and in the treatment of T-cell mediated autoimmune diseases such as rheumatoid arthritis and lupus.

U.S. Pat. Nos. 4,923,872, 4,988,702, and 5,061,707 which are herein incorporated by reference, disclose a novel series of pyrrolo[3,2-d]pyrimidines.

The compounds disclosed in U.S. Pat. Nos. 4,923,872, 4,988,702, and 5,061,707 are useful for treating autoimmune disease, gout, psoriasis, and rejection of transplantation. Particularly valuable in the aforementioned therapeutic categories is 2-amino-3,5-dihydro-7-(3-thienylmethyl)-4H-pyrrolo[3,2-d]pyrimidin-4-one. The aforementioned compound has been prepared by catalytic hydrogenation of 2-amino-1,6-dihydro-5-nitro-6-oxo-α-(3-thienylmethyl)-4-pyrimidineacetonitrile.

Church R. F. R., et al., *Journal of Organic Chemistry*, 36:723 (1971) disclosed the replacement of a diazonium salt with hydrogen using a palladium catalyst in the presence of formaldehyde. Thus, Church R. F. R., et al., hydrogenated the diazonium salt of 9-amino-7-nitro-6-demethyl-6-deoxytetracycline to afford 7-nitro-6-demethyl-6-deoxytetracycline. In a footnote the previous authors note that the replacement of the diazonium group by hydrogen by this procedure is unusual. This is the only literature disclosure of catalytic reduction of diazonium salts with a precious metal or Raney-type nickel catalyst to replace an amino group with hydrogen of which we are aware.

The object of the present invention is an improved process for preparing 2-amino-3,5-dihydro-7-substituted-4H-pyrrolo[3,2-d]pyrimidine-4-ones and in particular 2-amino-3,5-dihydro-7-(3-thienylmethyl)-4H-pyrrolo[3,2-d]pyrimidin-4-one from 2,6-diamino-3,5-dihydro-7-(3-thienylmethyl)-4H-pyrrolo[3,2-d]pyrimidin-4-one. The present method involves the replacement of an amino group with hydrogen through the diazonium salt by catalytic reduction over a precious metal or Raney-type nickel catalyst in an atmosphere of hydrogen. The present process uses hydrogen gas rather than formaldehyde. This has several advantages. The workup of hydrogenations is simpler than reactions using formaldehyde since hydrogen gas is released and the catalyst is removed by filtration; and formaldehyde is toxic, a possible carcinogen, a sensitizer, and an irritant which requires the use of special equipment and extensive personal protective gear.

Thus, we have surprisingly and unexpectedly found an improved process to prepare 2-amino-3,5-dihydro-7-substituted-4H-pyrrolo[3,2-d]pyrimidin-4-ones which uses less hazardous reagents and does not require chromatography to purify the product. Therefore, the present process is amenable to large-scale synthesis. It is also surprising that the 6-amino group and not the 2-amino group is selectively diazotized and replaced.

SUMMARY OF THE INVENTION

Accordingly, a first aspect of the present invention is an improved process for the preparation of a compound of Formula I

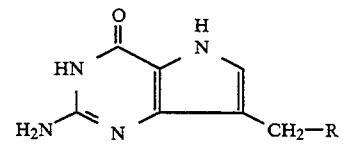

and pharmaceutically acceptable acid addition salts thereof wherein R is aryl or heteroaryl which comprises:

Step (a) treating a compound of Formula III

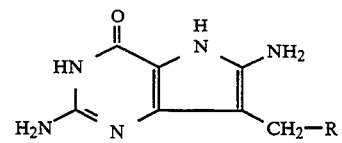

wherein R is as defined above with a diazotization reagent in a solvent to afford a compound of Formula II

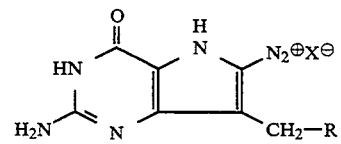

wherein X is Cl, Br, I, $BF_4$, $PF_6$, or $HSO_4$ and R is as defined above;

Step (b) treating a compound of Formula II with hydrogen in the presence of a catalyst and a solvent to afford a compound of Formula I;

Step (c) and, if desired, converting the resulting compound of Formula I to a corresponding pharmaceutically acceptable acid addition salt by conventional means, and if so desired, converting the corresponding pharmaceutically acceptable acid addition salt to a compound of Formula I by conventional means.

A second aspect of the present invention is a novel intermediate of Formula II

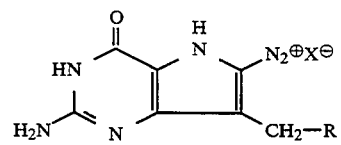

wherein X is Cl, Br, I, $BF_4$, $PF_6$, or $HSO_4$ and R is aryl or heteroaryl.

DETAILED DESCRIPTION OF THE INVENTION

In this invention, the term "alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

"Alkyl" means a straight or branched hydrocarbon radical having from one to six carbon atoms and includes, for example, methyl, ethyl, n-propyl, isopropyl, n-butyl, sec-butyl, isobutyl, tert-butyl, n-pentyl, n-hexyl, and the like.

"Aryl" means an aromatic radical which is a phenyl group, unsubstituted or substituted by 1 to 3 substituents selected from alkyl as defined above, trifluoromethyl, or halogen as hereinafter defined.

"Heteroaryl" means a heteroaromatic radical which is 2- or 3-thienyl, 2-furanyl, or 3-pyridinyl.

"Halogen" is fluorine, chlorine, bromine, or iodine.

A compound of Formula I is capable of further forming a pharmaceutically acceptable acid addition salt. All of these forms are within the scope of the present invention.

Pharmaceutically acceptable acid addition salts of a compound of Formula I include salts derived from nontoxic inorganic acids such as hydrochloric, nitric, phosphoric, sulfuric, hydrobromic, hydriodic, phosphorous and the like, as well as the salts derived from nontoxic organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate and the like. Also contemplated are salts of amino acids such as arginate and the like and gluconate, galacturonate (see, for example, Berge S. M., et al., "Pharmaceutical Salts," *Journal of Pharmaceutical Science*, 66:1-19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free bases for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

As previously described, the compounds of Formula I are useful as inhibitors of purine nucleoside phosphorylase and for treating autoimmune diseases, gout, psoriasis, and rejection of transplantation as disclosed in Montgomery J. A., et al., *Journal of Medicinal Chemistry*, 36:55-69 (1993); Secrist III J. A., et al., *Journal of Medicinal Chemistry*, 36:1847-1854 (1993); and in U.S. Pat. Nos. 4,923,872, 4,988,702, and 5,061,707.

The process of the present invention in its first aspect is a new, improved, economical, less hazardous, and commercially feasible method for preparing the compounds of Formula I. The process of the present invention in its first aspect is outlined in Scheme I.

SCHEME I

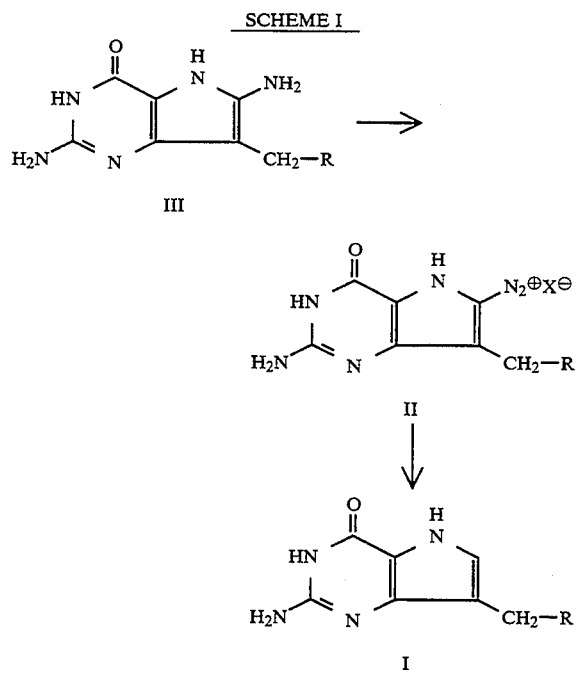

A compound of Formula III wherein R is aryl or heteroaryl is diazotized according to methods known in the art. For example, see Vogel A., *Textbook of Practical Organic Chemistry*, 4th Edition; Longman: London, 1978, p. 687; Patai S., *Chemistry of Diazonium and Diazo Groups*, Part 2, Wiley: Chichester, 1978, p. 555; Roe A., "Preparation of Aromatic Fluorine Compounds From Diazonium Fluoroborates, The Schiemann Reaction" in *Organic Reactions*, Vol. 5, Wiley: New York, 1949, p. 198.

The diazotization reaction is carried out with 1 to 2 equivalents of a diazotization reagent such as, for example, $MNO_2$ wherein M is an alkali metal such as, for example, sodium, potassium, and the like, or an alkyl nitrite or $HNO_2$ in the presence of an acid, such as, for example, HX wherein X is Cl, Br, I, $BF_4$, $PF_6$, $HSO_4$, and the like, or a metal salt such as, for example, M'X, wherein M' is an alkali metal such as, for example, sodium, potassium, lithium, and the like, or an alkaline earth metal such as, for example, magnesium, calcium, and the like or an ammonium ($NH_4^+$) salt and a solvent such as, for example, water, alcohols or mixtures thereof, and the like. Alternatively, other solvents such as, for example, dimethylformamide, tetrahydrofuran, polar aprotic solvents and the like may be used (Doyle M. P., et al., *Journal of Organic Chemistry*, 42:3494 (1977)) at a temperature of about −10° C. to about 40° C. for about 5 minutes to about 24 hours to afford a compound of Formula II wherein X is Cl, Br, I, $BF_4$, $PF_6$, or $HSO_4$. Preferably, the reaction is carried out with sodium nitrite and hydrochloric acid in water at about 0° C. to about 25° C. for about 15 minutes to about 3 hours.

A compound of Formula I wherein R is aryl or heteroaryl is prepared by treating a compound of Formula II with hydrogen at a pressure of about 10 to about 100 pounds per square inch gauge (psig) in the presence of a catalyst such as, for example, palladium, 5% palladium on carbon, platinum, rhodium, ruthenium, Raney-type nickel, and the like, and a solvent such as water, an alcohol or mixtures thereof, and the like at about 0° C. to about 50° C. for about 5 minutes to about 24 hours to afford a compound of Formula I. Preferably, the reaction is carried out in isopropanol and water with about 20 to about 60 psig of hydrogen in the presence of 5% palladium on carbon at about 0° C. to about 40° C. for about 15 minutes to about 5 hours.

Additionally, a compound of Formula I may be further purified to remove any starting material by treatment with up to 50% (molar basis) of sodium nitrite, preferably 10% and carbon, preferably 10–30% by weight, stirring at about 0° C. to about 50° C., preferably stirring at about 20° C. to about 30° C. for about 5 minutes to about 3 hours, preferably about 30 minutes to about 1.5 hours. The carbon is removed by filtration, washed with a solvent such as, for example, methanol, and the filtrate concentrated to afford the compound of Formula I. Recrystallization from HCl, carbon, and water, or mixtures of water and alcohols, acetone, acetonitrile, or tetrahydrofuran, preferably water or water and methanol to afford a compound of Formula I.

A compound of Formula III may be prepared by the methodology described in U.S. Pat. Nos. 4,923,872, 4,988,702, and 5,061,707.

The following nonlimiting examples illustrate the inventors' preferred method for preparing the compounds of Formula I according to the present process.

EXAMPLE 1

2-Amino-3,5-dihydro-7-(3-thienylmethyl)-4H-pyrrolo[3,2-d]pyrimidin-4-one, hydrochloride, monohydrate

Step A: Preparation of 2-Amino-4,5-dihydro-4-oxo-7-(3-thienylmethyl)-3H-pyrrolo[3,2-d]pyrimidine-6-diazonium chloride Charged 23.4 kg (74.1 mol) of 2,6-diamino-3,5-dihydro-7-(3-thienylmethyl)-4H-pyrrolo[3,2-d]pyrimidin-4-one, hydrochloride, monohydrate (U.S. Pat. No. 4,923,872), 240 L water and 14.9 kg (147.1 mol) 36% hydrochloric acid to a nitrogen-purged 800 L reactor. The resulting slurry is cooled to 0° C. A solution of 7.9 kg (114.5 mol) sodium nitrite in 20 L water is added to the slurry over 40 minutes. The reaction mixture is heated to 20° C. and held at that temperature for 1.3 hours. The product is collected and washed with 90 n water yielding 63.5 kg of the title compound as a water wet cake.

Step B: Preparation of 2-Amino-3,5-dihydro-7-(3-thienylmethyl)-4H-pyrrolo[3,2-d]pyrimidin-4-one, hydrochloride, monohydrate Charged 32 kg of water-wet 2-amino-4,5-dihydro-4-oxo-7-(3-thienylmethyl)-3H-pyrrolo[3,2-d]pyrimidine-6-diazonium chloride, 225 L isopropanol, 75 L water, 18.7 kg 36% hydrochloric acid, and 3.5 kg 5% palladium on carbon (50% water-wet) to a 400 L reactor. System is purged with nitrogen and hydrogen and reduced at 50 psig. The reaction mixture is filtered and the filter cake washed with 75 L isopropanol. The filtrate is transferred to a 2000 L reactor, diluted with 75 L of isopropanol, and cooled to 0° C. The remaining 31.5 kg of 2-amino-4,5-dihydro-4-oxo-7-(3-thienylmethyl)-3H-pyrrolo[3,2-d]pyrimidine-6-diazonium chloride is reduced in the same way, combining the filtrate with that from the first reduction. Seven and two-tenths kilograms ADP carbon, 4.0 kg Supercel, and 0.5 kg sodium nitrite is added to the filtrate and stirred I hour at 25° C. The mixture is filtered washing the cake with 200 L methanol. The filtrate is diluted with 260 L water and then vacuum distilled to a volume of 200 L. The resulting slurry is cooled to 0° C. and held at that temperature for 6.3 hours. The crude product is collected on a centrifuge and washed with 150 L cold water to yield 19.3 kg (14.9 kg on a dry basis from 2,6-diamino-3,5-dihydro-7-(3-thienylmethyl )-4H-pyrrolo[3,2-d]pyrimidin-4-one, hydrochloride, monohydrate) water-wet product as a tan solid.

Recrystallization

Nineteen and three-tenths kilograms water-wet, crude product is dissolved in 480 L water and 19.5 kg 36% hydrochloric acid at reflux. A slurry of 3.3 kg ADP carbon, and 2.0 kg Supercel in 20 L water is added to the solution and refluxed for 1.5 hours. The mixture is filtered hot washing the cake with 50 L hot water. The filtrate is cooled to 0° C. and held overnight. The product is collected on a centrifuge washing with 150 L water. Eighteen and seven-tenths kilograms of water-wet (12.7 kg dry), light tan-colored product is obtained of >99% purity. A second recrystallization from 520 L water, 15.3 kg hydrochloric acid, 1.3 kg ADP carbon, and 1 kg Supercel afforded 11.4 kg of product as pale yellow needles of >99% purity High Performance Liquid Chromatography (HPLC) (area %);

HPLC: 100.50% weight/weight against authentic reference material; Proton nuclear magnetic resonance spectroscopy.

($^1$H NMR)(DMSO-$d_6$): δ 12.7 (br s, 2H), 12.36 (d, J=2.8 Hz, 1H), 7.94 (s, 2H), 7.45 (dd, J=2.9, 4.9 Hz, 1H), 7.31 (m, 1H), 7.29 (d, J=2.8 Hz, 1H), 7.09 (dd, J=1.2, 4.9 Hz, 1H), 3.92 (s, 2H);

Carbon NMR ($^{13}$C NMR) (DMSO-$d_6$): δ 155.88, 151.12, 140.86, 130.64, 128.46, 127.47, 126.17, 121.24, 111.08, 110.07, 23.86.

In a process analogous to Example 1, the following compounds are prepared:

EXAMPLE 2

2-Amino-7-[(3,4-dichlorophenyl)methyl]-3,5-dihydro-4H-pyrrolo[3,2-d]pyrimidin-4-one

EXAMPLE 3

2-Amino-7-[(4-chlorophenyl)methyl]-3,5-dihydro-4H-pyrrolo[3,2-d]pyrimidin-4-one

EXAMPLE 4

2-Amino-7-[(3-fluorophenyl)methyl]-3,5-dihydro-4H-pyrrolo [3,2-d]pyrimidin-4-one

EXAMPLE 5

2-Amino-3,5-dihydro-7-[[3-(trifluoromethyl)pheny]methyl]-4H-pyrrolo[3,2-d]pyrimidin-4-one

EXAMPLE 6

2-Amino-3,5-dihydro-7-(phenylmethyl) -4H-pyrrolo [3,2-d]pyrimidin-4-one

EXAMPLE 7

2-Amino-3,5-dihydro-7-[(3-methylphenyl)methyl]-4H-pyrrolo [3,2-d]pyrimidin-4-one

EXAMPLE 8

2-Amino-7-[(2-chlorophenyl)methyl]-3,5-dihydro-4H-pyrrolo [3,2-d]pyrimidin-4-one

EXAMPLE 9

2-Amino-3,5-dihydro-7-(2-thienylmethyl)-4H-pyrrolo [3,2-d]pyrimidin-4-one

EXAMPLE 10

2-Amino-7-(2-furanylmethyl) -3,5-dihydro-4H-pyrrolo [3,2-d]pyrimidin-4-one

EXAMPLE 11

1-Amino-7-[(3-chlorophenyl)methyl]-3,5-dihydro-4H-pyrrolo [3,2-d]pyrimidin-4-one

EXAMPLE 12

2-Amino-3,5-dihydro-7-(3-pyridinylmethyl)-4H-pyrrolo[3,2-d]pyrimidin-4-one

We claim:

1. A process for the preparation of a compound of Formula I

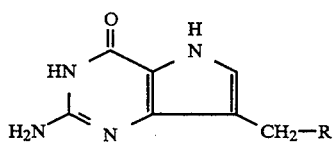

and pharmaceutically acceptable acid addition salts thereof wherein R is aryl or heteroaryl which comprises:

Step (a) treating a compound of Formula III

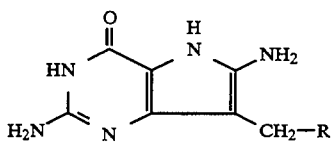

wherein R is as defined above with a diazotization reagent in a solvent to afford a compound of Formula II

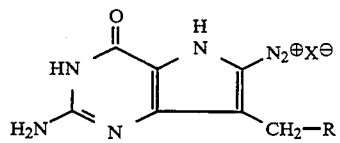

wherein X is Cl, Br, I, $BF_4$, $PF_6$, or $HSO_4$ and R is as defined above;

Step (b) treating a compound of Formula II with hydrogen in the presence of a catalyst and a solvent to afford a compound of Formula I;

Step (c) and, if desired, converting the resulting compound of Formula I to a corresponding pharmaceutically acceptable acid addition salt by conventional means, and if so desired, converting the corresponding pharmaceutically acceptable acid addition salt to a compound of Formula I by conventional means.

2. A process according to claim 1 wherein the diazotization reagent in Step (a) is selected from the group consisting of:

A] $MNO_2$ wherein M is an alkali metal, and an acid selected from the group consisting of: HCl, HBr, HI, $HBF_4$, $HPF_6$ and $H_2SO_4$ optionally in the presence of M'X wherein M' is an alkali metal, an alkaline earth metal or ammonium;

B] an alkyl nitrite and an acid selected from the group consisting of: HCl, HBr, HI, $HBF_4$, $HPF_6$ and $H_2SO_4$ optionally in the presence of M'X wherein M' is an alkali metal, an alkaline earth metal or ammonium; and C] $HNO_2$ and an acid selected from the group consisting of: HCl, HBr, HI, $HBF_4$, $HPF_6$ and $H_2SO_4$ optionally in the presence of M'X wherein M' is an alkali metal, an alkaline earth metal or ammonium.

3. A process according to claim 1 wherein in Step (b) the solvent is selected from the group consisting of: an alcohol; water; and mixtures thereof.

4. A process according to claim 2 wherein the acid is HCl.

5. A process according to claim 2 wherein $MNO_2$ is $NaNO_2$.

6. A process according to claim 1 wherein in Step (a) the solvent is selected from the group consisting of: water; water and alcohol; dimethylformamide; tetrahydrofuran; and mixtures thereof.

7. A process according to claim 6 wherein the solvent is water.

8. A process according to claim 1 wherein in Step (b) the catalyst is selected form the group consisting of: palladium, 5% palladium on carbon, platinum, rhodium, ruthenium, and Raney-type nickel.

9. A process according to claim 8 wherein the catalyst is 5% palladium on carbon.

10. A process according to claim 1 wherein in Step (b) the reaction is carried out at a pressure of about 10 to about 100 psig.

11. A process according to claim 10 wherein the reaction is carried out at a pressure of about 20 to about 60 psig.

12. A process according to claim 1 wherein in Step (b) the reaction is carried out at a temperature of about 0° C. to about 50° C.

13. A process according to claim 12 wherein the reaction is carried out at a temperature of about 0° C. to about 40° C.

14. A process according to claim 1 wherein in Step (b) the reaction is carried out for about 5 minutes to about 24 hours.

15. A process according to claim 14 wherein in Step (b) the reaction is carried out for about 15 minutes to about 5 hours.

16. A process according to claim 1 for the preparation of a compound selected from the group consisting of:
2-Amino-3,5-dihydro-7-(3-thienylmethyl)-4H-pyrrolo[3,2-d]pyrimidin-4-one;
2-Amino-7-[(3,4-dichlorophenyl)methyl]-3,5-dihydro-4H-pyrrolo[3,2-d]pyrimidin-4-one;
2-Amino-7-[(4-chlorophenyl)methyl]-3,5-dihydro-4H-pyrrolo[3,2-d]pyrimidin-4-one;
2-Amino-7-[(3-fluorophenyl)methyl]-3,5-dihydro-4H-pyrrolo[3,2-d]pyrimidin-4-one;
2-Amino-3,5-dihydro-7-[[3-(trifluoromethyl)phenyl]methyl]-4H-pyrrolo[3,2-d]pyrimidin-4-one;
2-Amino-3,5-dihydro-7-(phenylmethyl)-4H-pyrrolo[3,2-d]pyrimidin-4-one;
2-Amino-3,5-dihydro-7-[(3-methylphenyl)methyl]-4H-pyrrolo[3,2-d]pyrimidin-4-one;
2-Amino-7-[(2-chlorophenyl)methyl]-3,5-dihydro-4H-pyrrolo[3,2-d]pyrimidin-4-one;
2-Amino-3,5-dihydro-7-(2-thienylmethyl)-4H-pyrrolo[3,2-d]pyrimidin-4-one;
2-Amino-7-(2-furanylmethyl)-3,5-dihydro-4H-pyrrolo[3,2-d]pyrimidin-4-one;
1-Amino-7-[(3-chlorophenyl)methyl]-3,5-dihydro-4H-pyrrolo[3,2-d]pyrimidin-4-one; and
2-Amino-3,5-dihydro-7-(3-pyridinylmethyl)-4H-pyrrolo[3,2-d]pyrimidin-4-one.

17. A process according to claim 1 for the preparation of 2-amino-3,5-dihydro-7-(3-thienylmethyl)-4H-pyrrolo[3,2-d]pyrimidin-4-one.

18. A process according to claim 3 wherein the solvent is a mixture of isopropanol and water.

* * * * *